US007109154B2

(12) United States Patent
Abbas

(10) Patent No.: US 7,109,154 B2
(45) Date of Patent: Sep. 19, 2006

(54) COMBINATION TOILET BAR COMPOSITION

(75) Inventor: Syed Husain Abbas, Seymour, CT (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 225 days.

(21) Appl. No.: 10/823,528

(22) Filed: Apr. 13, 2004

(65) Prior Publication Data

US 2005/0227887 A1 Oct. 13, 2005

(51) Int. Cl.
*A61K 7/50* (2006.01)

(52) U.S. Cl. ...................... 510/141; 510/151; 510/152; 510/153; 510/155; 510/481; 510/491

(58) Field of Classification Search ................ 510/141, 510/151, 152, 153, 155, 492, 481, 491
See application file for complete search history.

(56) References Cited

U.S. PATENT DOCUMENTS

| | | | | |
|---|---|---|---|---|
| 5,264,145 | A * | 11/1993 | French et al. | 510/151 |
| 5,340,492 | A | 8/1994 | Kacher et al. | |
| 6,008,173 | A | 12/1999 | Chopra et al. | |
| 6,156,713 | A | 12/2000 | Chopra et al. | |
| 6,365,560 | B1 | 4/2002 | Chopra et al. | |

FOREIGN PATENT DOCUMENTS

| | | |
|---|---|---|
| WO | 95/26710 | 10/1995 |
| WO | 01/80820 | 11/2001 |

* cited by examiner

*Primary Examiner*—Necholus Ogden
(74) *Attorney, Agent, or Firm*—Alan A. Bornstein

(57) ABSTRACT

A combination toilet bar composition is described that contains soap, both amphoteric, and synthetic anionic surfactants in a specified ratio and a blend of hydrophobic emollients including a hydrocarbon with a titer of less than about 50 C. The toilet bar provides mild cleansing, moisturization, and creamy lather during use.

10 Claims, No Drawings

COMBINATION TOILET BAR COMPOSITION

BACKGROUND OF THE INVENTION

1. Field of the Invention

The present invention relates to a toilet bar suitable for moisturizing and cleansing the human body, such as the skin and hair. In particular, it relates to a toilet bar composition that is mild to the skin and which also has a creamy lather.

2. The Related Art

Combination toilet bars are well known. However, the majority of them are very irritating to the skin due to the fact that they are soap based, have low levels of moisturizers, or some combination thereof. Many prior art combination bars have been produced by using a co-surfactant along with some amount of free fatty acid to achieve a certain degree of mildness. The milder co-surfactants typically used along with the fatty acids provide a milder bar with creamy lather. Such co-surfactants typically used in combination bars are mainly sodium cocoyl isethionate, alfa olefin sulfonate, sodium lauryl sulfate or a similar type of synthetic surface active agent(s). The fatty acids often used as superfatting agents are mainly coco fatty acids or stearic/palmitic fatty acids. The fatty acids in combination bars or even superfatted bars have traditionally been used to generate the delta phase for improvement in lather and mush properties. In superfatted bars, the superfatting agents that have proven especially effective are low titer fatty acids which although not wishing to be bound by this theory, are believed to form the delta phase by their interaction with stearate/palmitate soaps.

It has been surprisingly found that a specific surfactant blend can be used as a co-surfactant along with a superfating mixture of both low and high titer fatty components in the inventive combination bar. At least one of the components of the co-surfactant mix is an amphoteric surfactant(s). The ratio of the non soap (synthetic) anionic to amphoteric surfactants can vary from 1:5 to 5:1 and the preferred total level of the cosurfactants is from 2–5%. The preferred anionic surfactant is selected from the group of C8–18 alkyl sulfo methyl ester or any of the C8–18 alkyl sulfate or sulfonate group of surfactants. Further, surprisingly it has been found that a mixture of emollients that are a combination of two or more of C8–18 alkyl fatty acids, fatty esters, fatty alcohols, triglycerides or hydrocarbons is more effective especially when a hydrocarbon with a titer less than 50 C is employed. In this case some of the fatty acid components can have titer as high as 70–80 C while the other emollient components can be having titer as low as 1–2 C.

SUMMARY OF THE INVENTION

In one aspect of the invention is a combination toilet bar, including but not limited to:

a. about 50 to 80% by wt. of soap(s); preferably having a lower limit of 60 or 70% by wt. and an upper limit of 68, 70 or 75%;
b. about 1 to 5% by wt. of amphoteric surfactant(s);
c. about 1 to 5 by wt. of synthetic anionic surfactant(s); preferably selected from C8 to C18 alpha olefin sulfonates, C8 to C14 acyl isethionates; C8 to C14 alkyl or alkyl ether sulfates, C8 to C14 alkyl sulfosuccinates, C8 to C14 alkyl sulfonates; C8 to C14 fatty acid ester sulfonates, derivatives, and blends thereof and the like;
d. about 0.1 to 10% of hydrophobic emollient(s) with a titer point between about 1 to 80 C other than a hydrocarbon with a titer less than about 50 C; preferably selected from C12–18 fatty acids, triglycercide oils, C12–18 esters and blends and derivatives thereof;
e. greater than about 0.1 to less than 2% by wt. of a hydrocarbon with a titer less than about 50 C;
f. wherein the ratio of synthetic anionic surfactants to amphoteric surfactant(s) is in the range of about 1 to 5 to 5 to 1; and
g. less than about 15% by wt. water.

In another aspect of the invention is a method of skin treatment and/or cleansing with a combination toilet bar, including but not limited to the steps of:

a. wetting the mild bar with water; the bar including:
   1. about 50 to 80% by wt. of soap(s); preferably having a lower limit of 60 or 70% by wt. and an upper limit of 68, 70 or 75%;
   2. about 1 to 5% by wt. of amphoteric surfactant(s);
   3. about 1 to 5 by wt. of synthetic anionic surfactant(s); preferably selected from alpha olefin sulfonates, alkyl and alkyl ether sulfates, mono and dialkyl sulfosuccinates and the like;
   4. about 0.1 to 10% of hydrophobic emollient(s) with a titer point between about 1 to 80 C other than a hydrocarbon with a titer less than about 50 C; (preferably selected from $C_{12-18}$ fatty acids, triglycercide oils, $C_{12-18}$ esters and blends and derivatives thereof)
   5. more than about 0.1% to less than 2% by wt. of a hydrocarbon with a titer less than about 50 C; and
   6. wherein the ratio of synthetic anionic surfactants to amphoteric surfactant(s) is in the range of about 1 to 5 to 5 to 1; and
b. rubbing the wet bar on the skin to deposit the emollients and/or skin active ingredients while cleansing the skin.

DETAILED DESCRIPTION OF THE INVENTION

In one aspect of the invention is a combination toilet bar, including but not limited to:

a. about 50 to 80% by wt. of soap(s); preferably having a lower limit of 60 or 70% by wt. and an upper limit of 68, 70 or 75%;
b. about 1 to 5% by wt. of amphoteric surfactant(s);
c. about 1 to 5 by wt. of synthetic anionic surfactant(s); preferably selected from C8 to C18 alpha olefin sulfonates, C8 to C14 acyl isethionates; C8 to C14 alkyl or alkyl ether sulfates, C8 to C14 alkyl sulfosuccinates, C8 to C14 alkyl sulfonates; C8 to C14 fatty acid ester sulfonates, derivatives, and blends thereof and the like;
d. about 0.1 to 10% of hydrophobic emollient(s) with a titer point between about 1 to 80 C other than a hydrocarbon with a titer less than about 50 C; preferably selected from C12–18 fatty acids, triglycercide oils, C12–18 esters and blends and derivatives thereof;
e. greater than about 0.1 to less than 2% by wt. of a hydrocarbon with a titer less than about 50 C;
f. wherein the ratio of synthetic anionic surfactants to amphoteric surfactant(s) is in the range of about 1 to 5 to 5 to 1; and
g. less than about 15% by wt. water.

Advantageously, the synthetic anionic surfactant has a Krafft point of less than about 30 C, preferably less than about 25, 20, 15, 10 or 5 C. Preferably the inventive bar further includes $C_{12-18}$ normal alkyl sulfonated methyl ester(s), preferably in the range of about 1 to 5 by wt.

In a preferred embodiment, the inventive bar further has a Lathering Index Ratio of more than about 0.8 and preferably more than about 1. Preferably cationic polymer(s), preferably in the concentration range of about 0.1 to 1% are used in the inventive bar. More preferably the bar has a pH of in the range of about 8.5 to 10.0, preferably a lower limit pH of about 8 and an upper limit of pH of about 9.5. Most preferably, the inventive bar further includes a safe and effective amount of at least one active agent, a hydrophilic moisturizing agent or blend thereof.

In a further preferred embodiment, the soaps include a blend of $C_6$ to $C_{22}$ alkyl soaps. Advantageously, the bar contains water in the range of about 1 to less than about 15% by wt., preferably in the range of about 8 to 12% by wt.

In another aspect of the invention is a method of skin treatment and/or cleansing with a combination toilet bar, including but not limited to the steps of:

a. wetting the mild bar with water; the bar including:
   1. about 50 to 80% by wt. of soap(s); preferably having a lower limit of 60 or 70% by wt. and an upper limit of 68, 70 or 75%;
   2. about 1 to 5% by wt. of amphoteric surfactant(s);
   3. about 1 to 5 by wt. of synthetic anionic surfactant(s); preferably selected from alpha olefin sulfonates, alkyl and alkyl ether sulfates, mono and dialkyl sulfosuccinates and the like;
   4. about 0.1 to 10% of hydrophobic emollient(s) with a titer point between about 1 to 80 C other than a hydrocarbon with a titer less than about 50 C; (preferably selected from $C_{12-18}$ fatty acids, triglyceride oils, $C_{12-18}$ esters and blends and derivatives thereof)
   5. more than about 0.1% to less than 2% by wt. of a hydrocarbon with a titer less than about 50 C; and
   6. wherein the ratio of synthetic anionic surfactants to amphoteric surfactant(s) is in the range of about 1 to 5 to 5 to 1; and b. rubbing the wet bar on the skin to deposit the emollients and/or skin active ingredients while cleansing the skin.

Surfactants:

Surfactants are an essential component of the inventive toilet bar. They are compounds that have hydrophobic and hydrophilic portions that act to reduce the surface tension of the aqueous solutions they are dissolved in. Useful surfactants can include soap(s), and non-soap anionic, nonionic, amphoteric, and cationic surfactants, and blends thereof.

Anionic Surfactants:

Soaps.

The inventive toilet bar contains soap, preferably it contains at least about 50% by wt. of soap. The term "soap" is used herein in its popular sense, i.e., the alkali metal or alkanol ammonium salts of alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be ammonium, potassium, magnesium, calcium or a mixture of these soaps. The soaps useful herein are the well known alkali metal salts of alkanoic or alkenoic acids having about 12 to 22 carbon atoms, preferably about 12 to about 18 carbon atoms. They may also be described as alkali metal carboxylates of alkyl or alkene hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range. It is preferred to use soaps having the fatty acid distribution of tallow, and vegetable oil. More preferably the vegetable oil is selected from the group consisiting of palm oil, coconut oil, palm kernal oil, palm stearin, and hydrogenated rice bran oil, or mixtures thereof, since these are among the more readily available fats. Especially preferred is coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12–18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter. A preferred soap is a mixture of about 15% to about 30% coconut oil and about 70% to about 85% tallow. These mixtures contain about 95% fatty acids having about 12 to about 18 carbon atoms. As mentioned above, the soap may preferably be prepared from coconut oil, in which case the fatty acid content is about 85% of $C_{12}$–$C_{18}$ chain length. The soaps may contain unsaturation in accordance with commercially acceptable standards. Excessive unsaturation is normally avoided. Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Synthetic Anionic Surfactants

The toilet bar of the present invention contains one or more non-soap anionic detergents (syndets). Preferably the syndets have a zein value of 50 or less. Zein value may be measured using the test method described below. Advantageously non-soap anionic detergents or surfactants are used from about 0.1, 0.2, 0.5, 1 or 2% by wt. to about 4, 5, 7, or 10% by wt.

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates having the formula:

$R^4O_2CCH_2CH(SO_3M)CO_2M$; and amide-MEA sulfosuccinates of the formula;

$R^4CONHCH_2CH_2O_2CCH_2CH(SO_3M)CO_2M$ wherein $R^4$ ranges from $C_8$–$C_{22}$ alkyl and M is a solubilizing cation.

Sarcosinates are generally indicated by the formula:

$R^1CON(CH_3)CH_2CO_2M$, wherein $R^1$ ranges from $C_8$–$C_{20}$ alkyl and M is a solubilizing cation.

Taurates are generally identified by formula:

$R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

The inventive skin care or cleansing composition may contain $C_8$–$C_{14}$ acyl isethionates. These esters are prepared by reaction between alkali metal isethionate with mixed aliphatic fatty acids having from 6 to 12 carbon atoms and an iodine value of less than 20.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

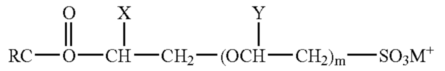

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Amphoteric Surfactants

One or more amphoteric surfactants are used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

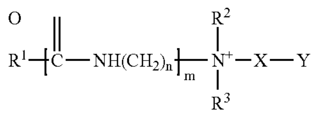

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3$

Suitable amphoteric surfactants within the above general formula include simple betaines of formula:

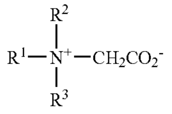

and amido betaines of formula:

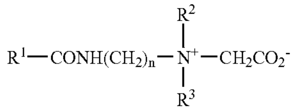

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

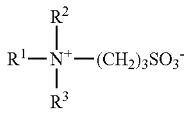 or 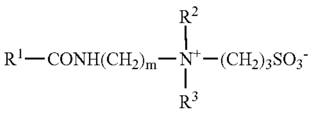

where m is 2 or 3, or variants of these in which $—(CH_2)_3SO_3^-$ is replaced by

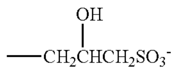

In these formulae $R^1$, $R^2$ and $R^3$ are as discussed previously.

Amphoacetates and diamphoacetates are also intended to be covered in the zwitterionic and/or amphoteric compounds which are used such as e.g., sodium lauroamphoacetate, sodium cocoamphoacetate, and blends thereof, and the like.

Nonionic Surfactants

One or more nonionic surfactants may also be used in toilet bar composition of the present invention. When present, nonionic surfactants may be used at levels as low as 0.1% and as high as 10%. The most preferable range is 2–5%.

The nonionics which may be used include in particularly the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Skin Conditioning Agents

An optional component in compositions according to the invention is a cationic skin feel agent or polymer, such as for example cationic celluloses. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200, and quaternary ammonium compounds such as alkyldimethylammonium halogenides.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art may be used provided that they are compatible with the inventive formulation.

Other preferred cationic compounds that are useful in the present invention include amido quaternary ammonium compounds such as quaternary ammonium propionate and lactate salts, and quaternary ammonium hydrolyzates of silk or wheat protein, and the like. Many of these compounds can be obtained as the Mackine™ Amido Functional Amines, Mackalene™ Amido functional Tertiary Amine Salts, and Mackpro® cationic protein hydrolysates from the McIntyre Group Ltd. (University Park, Ill.).

In a preferred embodiment of the invention having a hydrolyzed protein conditioning agent, the average molecular weight of the hydrolyzed protein is preferably about 2500. Preferably 90% of the hydrolyzed protein is between a molecular weight of about 1500 to about 3500. In a preferred embodiment, MACKPRO™ WWP (i.e. wheat germ amido dimethylamine hydrolyzed wheat protein) is added at a concentration of 0.1% (as is) in the bar. This results in a MACKPRO™ WWP "solids" of 0.035% in the final bar formula for this embodiment.

Cationic Surfactants

One or more cationic surfactants may also be used in the inventive toilet bar composition. When present, cationic surfactants may be used at levels as low as 0.1% and as high as 2.0%. The most preferred range is from 1–1.5%.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar., 27, 1973; and "Surface Active Agents and Detergents" (Vol. I & II) by Schwartz, Perry & Berch, both of which are also incorporated into the subject application by reference.

In addition, the inventive composition, especially the toilet bar of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Skin conditioning agents such as emollients are advantageously used in the present invention. Hydrophilic emollients including humectants such as polyhydric alcohols, e.g. glycerin and propylene glycol, and the like; polyols such as the polyethylene glycols listed below, and the like and hydrophilic plant extracts may be used. When used, humectants may be employed at levels greater than about 0.01, 0.05, 0.1, 0.2, 0.5, 0.9, 1, 1.1 or 2% by wt. The most preferred level is about 1.0–1.5% by wt.

| | |
|---|---|
| Polyox WSR-205 | PEG 14M, |
| Polyox WSR-N-60K | PEG 45M, or |
| Polyox WSR-N-750 | PEG 7M. |

Hydrophobic emollients are used in the inventive toilet bar. Preferably, hydrophobic emollients are used in excess of hydrophilic emollients. Hydrophobic emollients are preferably present in a concentration greater than about 0.01, 0.05, 0.1, 0.2, 0.5, 0.9, 1.0, 1.1, 2.0, 3.0, 5 or 10% by wt. The most preferred range is about 2–5% by wt. The term "emollient" is defined as a substance which softens or improves the elasticity, appearance, and youthfulness of the skin (stratum corneum) by increasing its water content, and keeps it soft by retarding the decrease of its water content.

Useful hydrophobic emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic plant extracts;

(e) hydrocarbons such as liquid paraffin, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils; and (j) mixtures of any of the foregoing components, and the like.

Preferred hydrophilic emollient moisturizing agents are selected from fatty acids, triglyceride oils, mineral oils, petrolatum, and mixtures thereof.

Krafft Point

The Krafft point of a surfactant is defined as the temperature (or more precisely, the narrow temperature range) above which the solubility of a surfactant rises sharply. At this temperature the solubility of the surfactant becomes equal to the critical micelle concentration. It may be determined by locating the abrupt change in slope of a graph of the logarithm of the solubility against temperature or 1/T or can be rapidly estimated using the the rapid estimation procedure described below. High Krafft point surfactants are defined as those that have a Krafft point above 30 C and low Krafft point surfactants are defined as those that have a Krafft point equal to or below 30 C using the rapid estimation technique below.

Exfoliants

The inventive toilet bar may contain particles that are greater than 50 microns in average diameter that help remove dry skin. Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc; crushed shells such as almond and walnut shells; oatmeal; polymers such as polyethylene and polypropylene beads, flower petals and leaves; microcrystalline wax beads; jojoba ester beads, and the like. These exfoliants come in a variety of particle sizes and morphology ranging from micron sized to a few mm. They also have a range of hardness. Some examples are given in table 1 below.

TABLE 1

| Material | Hardness (Mohs) |
|---|---|
| Talc | 1 |
| Calcite | 3 |
| Pumice | 4–6 |
| Walnut Shells | 3–4 |
| Dolomite | 4 |
| Polyethylene | ~1 |

Optional Active Agents

Advantageously, active agents other than skin conditioning agents defined above may be added to the toilet bar. These active ingredients may be advantageously selected from bactericides, vitamins, anti-acne actives; anti-wrinkle, anti-skin atrophy and skin repair actives; skin barrier repair actives; nonsteroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; or mixtures thereof; and the like.

These active agents may be selected from water soluble active agents, oil soluble active agents, pharmaceutically-acceptable salts and mixtures thereof. The term "active agent" as used herein, means personal care actives which can be used to deliver a benefit to the skin and/or hair and which generally are not used to confer a skin conditioning benefit, such are delivered by emollients as defined above. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the compositions of the present invention comprise from about 0.01% to about 50%, more preferably from about 0.05% to about 25%, even more preferably 0.1% to about 10%, and most preferably 0.1% % to about 5%, by weight of the active agent component.

A wide variety of active agent ingredients are useful herein and include those selected from anti-acne actives, anti-wrinkle and anti-skin atrophy actives, skin barrier repair aids, cosmetic soothing aids, topical anesthetics, artificial tanning agents and accelerators, skin lightening actives, antimicrobial and antifungal actives, sunscreen actives, sebum stimulators, sebum inhibitors, anti-glycation actives and mixtures thereof and the like.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4,4'-trichloro-2'-hydroxy diphenyl ether, 3,4,4'-Trichlorocarbanilide (triclocarban), phenoxyethanol, 2,4,4'-Trichloro-2'-Hydroxy Diphenyl Ether (triclosan); and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Nonlimiting examples of skin barrier repair actives include lipids such as cholesterol, ceramides, sucrose esters and pseudo-ceramides as described in European Patent Specification No. 556,957; ascorbic acid; biotin; biotin esters; phospholipids, mixtures thereof, and the like.

Non-steroidal Cosmetic Soothing Actives can be effective in preventing or treating inflammation of the skin. The soothing active enhances the skin appearance benefits of the present invention, e.g., such agents contribute to a more uniform and acceptable skin tone or color. Nonlimiting examples of cosmetic soothing agents include the following categories: propionic acid derivatives; acetic acid derivatives; fenamic acid derivatives; mixtures thereof and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Nonlimiting examples of skin lightening actives useful herein include aloe extract, alpha-glyceryl-L-ascorbic acid, aminotyroxine, ammonium lactate, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of octyl methoxyl cinnamate (Parsol MCX) and butyl methoxy benzoylmethane (Parsol 1789), 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful as active ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl (meth)acrylates, mixtures thereof, and the like.

Active ingredients in the present invention may also include anti-itch ingredients. Suitable examples of anti-itch ingredients which are useful in the compositions of the present invention include hydrocortisone, methdilizine and trimeprazineare, mixtures thereof, and the like.

Nonlimiting examples of hair growth inhibitors which are useful in the compositions of the present invention include 17 beta estradiol, anti angiogenic steroids, curcuma extract, cycloxygenase inhibitors, evening primrose oil, linoleic acid and the like. Suitable 5-alpha reductase inhibitors such as ethynylestradiol and, genistine mixtures thereof, and the like.

Nonlimiting examples of desquamating enzyme enhancers which are useful in the compositions of the present invention include alanine, aspartic acid, N methyl serine, serine, trimethyl glycine, mixtures thereof, and the like.

A nonlimiting example of an anti-glycation agent which is useful in the compositions of the present invention would be Amadorine (available from Barnet Products Distributor), and the like.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below:

The following inventive toilet bars may be formulated according to the manufacturing methods described below:

EXAMPLE 1

Combination Toilet Soaps

A comparative toilet bar(A) and three examples of inventive combination bars (B, C and D) were prepared and their latherability indices and skin visual dryness were measured (see Table 2) according to the methods described below. The inventive bars are seen to provide equivalent lathering properties in comparison to the formulation control (A) with 20% by wt. of sodium cocoyl isethionate but are further seen to be milder.

TABLE 2

| Ingredients % by wt. (active basis except as noted) | A | B | C | D |
|---|---|---|---|---|
| 70/30 Tallow/Coco Soap | 53.30 | 73.20 | 73.50 | 71.5 |
| Sodium Cocoyl Isethionate | 20.00 | — | — | — |
| Sodium Isethionate | 4.00 | — | — | — |
| Coco Fatty Acid | 1.00 | 0.50 | 0.50 | — |
| Stearic Acid | 7.00 | 5.00 | 5.00 | 8.00 |
| Petrolatum | — | 1.00 | 1.00 | 1.00 |
| Mineral Oil | — | 0.50 | 0.50 | — |
| Sunflower Seed Oil | 0.50 | 0.50 | 0.50 | 0.50 |
| Perfume | 1.30 | 1.30 | 1.30 | 1.30 |
| Merquat 100 (40% Soln) | — | 0.20 | — | — |
| Wheat Protein (33% Soln) | — | 0.10 | — | — |
| Sodium Chloride | 0.80 | 1.30 | 1.30 | 1.30 |
| Glycerin | — | 0.50 | 0.50 | 0.50 |
| Titanium Dioxide | 0.60 | 0.60 | 0.60 | 0.60 |
| Alkyl C12–18 Sulfomethyl Ester | — | 2.00 | 2.00 | 2.00 |
| Cocoamidopropyl betaine | — | 1.80 | 1.80 | 1.80 |
| Water | 11.50 | 11.50 | 11.5 | 11.50 |
| Total (%) | 100 | 100 | 100 | 100 |
| Lather Index Ratio | 1.0 | 0.95 | 1.0 | 0.95 |
| PH | 9.0 | 9.3 | 9.3 | 9.25 |
| Transepidermal Water Loss (mean change from baseline after 5 days) | 3.59 | 3.37 | 3.06 | 2.77 |

Method of Making the Formulations:

The surfactant blends are made separately or the individual surfactants are directly injected in the neat soap at the required level. Similarly the superfat/emollient blend is injected directly in the neat soap or the individual superfatting/emollient ingredients are injected in the neat soap before drying. All the ingredients can be added through neat soap except color and fragrance. These components can be added in the chip mixer along with the soap noodles then mixed, plodded and stamped in the form of bars. Some of the superfatting/ emollient ingredients can be added in the chip mixer instead of injecting in the neat soap.

EXAMPLE 2

Inventive bars E –H may also be prepared as illustrated in Table 3.

TABLE 3

| | BARS | | | |
|---|---|---|---|---|
| Ingredients (% by wt. active) | E | F | G | H |
| 70/30 Soap (tallow/coco) | 65.30 | 70.80 | 73.7 | 70.0 |
| Coco Fatty Acid | 0.5 | 0.50 | 0.50 | — |
| Stearic Acid | 5.00 | 5.00 | 5.00 | 8.00 |
| Petrolatum | 1.0 | 1.00 | 1.00 | 1.00 |
| Kaolin | 5 | — | — | — |
| Mineral Oil | 0.5 | 0.50 | 0.50 | — |
| Sunflower Seed Oil | 0.5 | | | |
| Perfume | 1.30 | 1.30 | 1.30 | 1.30 |
| Green Tea Extract | 0.2 | 0.20 | — | — |
| Wheat Protein (33% Soln) | — | — | 0.10 | — |
| Sodium Chloride | 1.3 | 1.30 | 1.30 | 1.30 |
| Glycerin | 0.5 | 0.50 | 0.50 | — |
| Titanium Dioxide | 0.60 | 0.60 | 0.60 | 0.60 |
| Tapioca Starch | | | | 0.50 |
| Alkyl $C_{12-18}$ Sulfomethyl Ester | 5.0 | 5.00 | 1.00 | 3.00 |
| Cocoamido propyl betaine | 1.8 | 1.80 | 3.00 | 2.80 |
| Water | 11.50 | 11.50 | 11.5 | 11.50 |
| TOTAL (%) | 100 | 100 | 100 | 100 |

DESCRIPTION OF TEST METHODS

Methods of Testing a) Latheribility Index Test

The latherability index of toilet bars are determined by using the Lather Index Ratio. Formula A is taken as control for the relative evaluation. Lather Index Ratio is the ratio of the lather generated by the inventive example to the control (Bar A). Lather volume is measured by using a water displacement method. In this method the wet bar is rotated for 5 times in wet hands and then about 10 ml water (at about 30 C) is taken in the hand. Lather is generated in the hand by rubbing both the hands against each other. Both the hands are dipped in water under an inverted funnel. The generated lather is collected by the inverted funnel and quantified via an attached graduated cylinder. Lather volume is measured in mls at about 30 C.

b) Titer Method (for Superfatting Agents/Emollients)

For the hydrophobic emollients with a titer more than room temperature, a small quantity of emollient is transferred to a glass capillary that is sealed on one side and the capillary is attached to the bulb of a thermometer. The capillary attached to the thermometer is dipped in water in a glass beaker. The water in the glass beaker is slowly heated and the temperature of the water is recorded by the thermometer attached to the capillary. The titer of the material is the temperature at which the emollient or superfatting agent is observed to start melting.

c) Krafft Point Determination

Make up a 10% by wt. solution of surfactant in water. If needed, heat the system to dissolve the surfactant completely. Transfer the clear solution to a glass test tube. Place the test tube in a beaker equipped with a stirrer and filled with sufficient water to evenly cool the surfactant solution.

The solution should be cooled with continuous stirring and the temperature should be continuously recorded. Note the temperature when the crystallization process begins such that the solution becomes turbid. This temperature is taken as the Krafft point. If the crystallization temperature is below room temperature, add ice to the beaker to cool the test tube below room temperature to measure the subambient Krafft point.

d) Mildness Test:

i) The mildness of the inventive toilet bars was assessed by the Forearm Controlled Application Test (FCAT) Clinical Test Methodology as follows:

This controlled washing test is similar to that described by Ertel et al (A forearm controlled application technique for estimating the relative mildness of personal cleansing products, J. Soc. Cosmet. Chem., 46, 67 (1995)).

Subjects report to the testing facility for the conditioning phase of the study, which consists of using an assigned marketed personal washing cleanser for general use at home, up to four days prior to start of the product application phase. On Day 1 of the product application phase, a visual assessment is made to determine subject qualification. Subjects must have dryness scores >1.0 and erythema scores >0.5, and be free of cuts and abrasions on or near the test sites to be included in the product application phase. Subjects who qualify to enter the product application phase will then be instructed to discontinue the use of the conditioning product and any other skin care products on their inner forearms, with the exception of the skin cleansing test formulations that are applied during the wash sessions.

Qualified subjects will then have four 3.0-cm diameter (round) evaluation sites marked on each of the forearms using a skin safe pen (a total of eight sites). Visual evaluations for erythema and dryness will be conducted immediately prior to the first wash in each session and again in the afternoon of the final day (Day 5).

Washing Procedure for Bar Products

1. Both arms are washed simultaneously. Test sites are treated in a sequential manner starting with the site closest to the flex area, ending with the site proximal to the wrist.
2. The sites closest to the flex area of the inner forearm of both the right and left arm are moistened with warm water (90°–100° F.).
3. A moistened Masslinn towel is rubbed in a circular motion on a wetted test bar for approximately 6 seconds by study personnel which will result in 0.20.5 g of product to be dispensed.
4. The site is washed with the designated product for 10 seconds followed by a 90-second lather retention phase.
5. The above procedure (1–4) is then repeated for each of the test sites. Sites are then be rinsed (e.g. using a temperature of 35° C.) for fifteen seconds and patted dry.
6. Upon completion the entire procedure is repeated (two washes/session).

Evaluation Methods

Baseline visual assessments are made prior to the start of the product application phase, and immediately before each wash session thereafter, to evaluate dryness and erythema. The final visual evaluation is conducted on the afternoon of the final day.

The 0–6 grading scale shown in Table 4 is used to assess the test sites for dryness and erythema. To maintain the evaluator's blindness to product assignment, visual assessments are conducted in a separate area away from the product application area.

TABLE 4

Erythema and Dryness grading scale.

| Grade | Erythema | Dryness |
|---|---|---|
| 0 | None | None |
| 1.0 | Barely perceptible | Patches of slight powderiness and redness occasional patches of small scales may be seen. Distribution generalized. |
| 2.0 | Slight redness | Generalized slight powderiness. Early cracking or occasional small lifting scales may be present |
| 3.0 | Moderate redness | Generalized moderate powderiness and/or heavy cracking and lifting scales. |
| 4.0 | Heavy or substantial | Generalized heavy powderiness and/or redness heavy cracking and lifting scales |
| 5.0 | Extreme redness | Generalized high cracking and lifting scales. Powderiness may be present but not prominent. May see bleeding cracks. |
| 6.0 | Severe redness | Generalized severe cracking. Bleeding cracks. Bleeding cracks may be present. Scales large, may be beginning to disappear. |

Instrumental readings are taken on the first (baseline) and final day of the study.

Mildness of test product is calculated as 1/(mean change in dryness at end of the study).

In addition to visual evaluation, instrumental assessments of the treated sites will be conducted using an evaporimeter and skin conductance meter as described in the reference above.

Instrumental Assessment

All instrumental evaluations will be taken following a 30-minute acclimation period. The indoor humidity and temperature data will be recorded and included in the final report. Instrumental measurements may be taken at some or all of the following time points: 0, 1, 2, 4, 6, 8 and 24 hours after product application. Instruments to be used with this protocol include: The Derma Lab Model #CR 200001-140, ServoMed Evaporimeter with EP1 or EP2 probe, Corneometer CM820, the Skicon Skin Hygrometer with the MT-8C probe, and the Moisture Checker. The room temperature will be maintained at 20° to 25° C. and 30% to 40% Relative Humidity. Moisturization is defined as mean change from baseline of visual dryness or skin hydration.

Transepidermal Water Loss Test (TEWL)

The Derma Lab Model #CR 200001-140 was used to quantify the rates of transepidermal water loss following the procedures similar to those outlined by Murahata et al ("The use of transepidermal water loss to measure and predict the irritation response to surfactants" Int. J. Cos. Science 8, 225 (1986)). TEWL provides a quantitative measure of the integrity of the stratum corneum barrier function and the relative effect of cleansers.

The operating principle of the instrument is based on Fick's law where $$(1/A)(dm/dt)=-D\ (dp/dx)$$

where

A=area of the surface (m 2)

m=weight of transported water (g)

t=time (hr)

D=constant, 0.0877 g-1 h-1 (mm Hg)-1 related to the diffusion coefficient of water p=partial pressure of water vapor in air (mm Hg)

x=distance of the sensor from the skin surface (m)

The evaporation rate, dm/dt, is proportional to the partial pressure gradient, dp/dx. The evaporation rate can be determined by measuring the partial pressures at two points whose distance above the skin is different and known, and where these points are within a range of 15–20 mm above the skin surface. The general clinical requirements are as follows:

1. All panelists are equilibrated for a minimum of fifteen minutes before measurements in a test room in which the temperature and relative humidity are controlled.
2. The test sites are measured or marked in such a way that pre and post treatment measurements can be taken at approximately the same place on the skin.
3. The probe is applied in such a way that the sensors are perpendicular to the test site, using a minimum of pressure.

Probe Calibration is achieved with a calibration set (No. 2110) which is supplied with the instrument. The kit must be housed in a thermo-insulated box to ensure an even temperature distribution around the instrument probe and calibration flask.

The three salt solution used for calibration are LiCl, [MgNO 3] 2, and K 2 SO 4. Pre-weighed amounts of slat at high purity are supplied with the kit instrument. The solution concentrations are such that the three solutions provide a RH of Ã11.2%, Ã54.2%, and Ã97% respectively at 21° C.

General Use of the Instrument is as Follows:

1. For normal studies, instrument readings are taken with the selector switch set for 1–100 g/m2 h range
2. The protective cap is removed from the probe and the measuring head is placed so that the Teflon capsule is applied perpendicularly to the evaluation site ensuring that a minimum pressure is applied from the probe head. To minimize deviations of the zero point, the probe head should be held by the attached rubber-insulating stopper.
3. Subject equilibration time prior to prior to evaluation is 15 minutes in a temperature/humidity controlled room.
4. The probe is allowed to stabilize at the test site for a minimum of 30 seconds before data acquisition. When air drafts exist and barrier damage is high it is recommended to increase the stabilization time.
5. Data is acquired during the 15 seconds period following the stabilization time.

Skin Hydration Test

The Corneometer CM802PC (Courage & Khazaha, Kohl, Germany) is a device widely used in the cosmetic industry. It allows high frequency, alternating voltage electrical measurements of skin capacitance to be safely made via an electrode applied to the skin surface. The parameters measured have been found to vary with skin hydration. However, they may also vary with many other factors such as skin temperature, sweat gland activity, and the composition of any applied product. The Corneometer can only give directional changes in the water content of the upper stratum corneum under favorable circumstances but even here the quantitative interpretations may prove misleading.

A widely used alternative is the Skicon Skin conductance Meter (I.B.S. Co Ltd. Shizuoka-ken, Japan).

Panelist Requirements for Either Instrument are as Follows:

1. Subjects should equilibrate to room conditions, which are maintained at a fixed temperature and relative humidity for a minimum of 15 minutes with their arms exposed. Air currents should be minimized.
2. Physical and psychological distractions should be minimized, e.g., talking and moving around.
3. Consumption during at least 1 hour before measurement of hot beverages or of any products containing caffeine should be avoided.
4. Panelists should avoid smoking for at least 30 minutes prior to measurements.

Operating Procedure

1. The probe should be lightly applied so as to cause minimum depression of the skin surface by the outer casing. The measuring surface is spring-loaded and thus the probe must be applied with sufficient pressure that the black cylinder disappears completely inside the outer casing.
2. The probe should be held perpendicular to the skin surface.
3. The operator should avoid contacting hairs on the measure site with the probe.
4. The probe should remain in contact with the skin until the instrument's signal beeper sounds (about 1 second) and then be removed. Subsequent measurements can be made immediately provided the probe surface is known to be clean.
5. A minimum of 3 individual measurements should be taken at separate points on the test area and averaged to represent the mean hydration of the site.
6. A dry paper tissue should be used to clean the probe between readings.

e) Moisturizer Deposition Test:

Precondition the subject's skin (arms/legs) with non-moisturizer containing product for up to 2 days prior to testing. A baseline extraction is performed to estimate level of moisturizer (e.g.: fatty acids) present on the skin prior to product application. Controlled single application of product to skin (arms or legs) is made. For wash, bar is rubbed on skin for 30 sec. and the lather left on for 90 sec., rinsed for 30 sec. (e.g. using a temperature of 35 C) then gently pat dry. Following this, the site is extracted using a suitable solvent (IPA)/methanol 1:1). The extraction is performed as follows: A glass cup (3 cm diameter) is placed on the skin. 3 mls of solvent is placed into this and gently stirred with a glass rod for 2 minutes. The solvent is removed with a pipette. This step is repeated with a fresh 3 mls of solvent, to collect a total of 6 mls extract. The extracts are analyzed for stearic acid/palmitic acid content using either LC/MS or GC/MS, or the like.

f) Skin Abrasiveness Test

Skin abrasiveness is defined as consumer rated response of abrasivity on a 0–9 scale (0 means no abrasion, 10 is abrasivity caused by a pouf (i.e. a showering implement composed of thin plastic filaments, see also e.g. U.S. Pat. No. 5,650,384 to Gordon et al.).

This test is performed with 50 untrained consumers. They are asked to rate the abrasiveness of the test product on a 0–9 point scale. The data is normalized based on their response to a bar with no exfoliants which is assigned a value of zero and a pouf that is assigned a value of 9. The test products are applied to the flex area of the forearm by wetting the bar and rubbing back and forth 10–15 times.

g) pH Test Method

Form an aqueous slurry by blending 10 grams of the bar formula with 90 g of water to create a 10% slurry. The pH of the slurry is then measured at 25 C.

h) Zein Test Method

The inventive toilet bar preferably has a zein solubility of under about 50, 40, 30, and most preferably under about 25 using the zein solubility method set forth below. The lower the zein score, the milder the product is considered to be. This method involves measuring the solubility of zein (corn protein) in cleansing base solutions as follows:

0.3 g of cleansing base and 29.7 g of water at room temperature (25C).

are mixed thoroughly. To this is added 1.5 g of zein, and mixed for 1 hour. The mixture is then centrifuged for 30 minutes at 3000 rpm. After centrifugation, the pellet is extracted, washed with water, and dried in a vacuum oven for 24 hours until substantially all the water has evaporated. The weight of the dried pellet is measured and percent zein solubilized is calculated using the following equation:

% Zein solubilized=100 (1-weight of dried pellet/1.5).

The % Zein is further described in the following references: E. Gotte, Skin compatibility of tensides measured by their capacity for dissolving zein protein, Proc. IV International Congress of Surface Active Substances, Brussels, 1964, pp 83–90.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

i) Patch Testing

A 48 hr continuous or 14 day cumulative insult patch test may be used: In the 48 hr patch test 5–15% solution/slurry of the product is applied onto the upper arm/back of the subject using a standard cotton pad. Irritation response is recorded for up to 24 hrs after removal of the patch. In the 14 day cumulative test a 5–15% solution/slurry of the product is applied repeatedly every 24 hrs for 14 days. Irritation response is recorded for up to 24 hrs after removal of patch.

Mildness of test product is evaluated as 1/(mean erythema at 24 hr after final patch removal).

What is claimed is:

1. A combination toilet bar, comprising:

a. about 50 to 80% by wt. of soap(s) wherein the soap(s) contain 15.6–24.9% by wt. of oleic soap;

b. about 1 to 5% by wt. of amphoteric surfactant(s);

c. about 1 to 5 by wt. of synthetic anionic surfactant(s);

d. about 0.1 to 10% of hydrophobic emollient(s) with a titer point between about 1 to 80 C other than a hydrocarbon with a titer less than about 50 C;

e. greater than about 0.1 to less than 2% by wt. of a hydrocarbon with a titer less than about 50 C;

f. wherein the ratio of synthetic anionic surfactants to amphoteric surfactant(s) is in the range of about 1 to 5 to 5 to 1; and g. less than about 15% by wt. water.

2. The bar of claim 1 wherein the synthetic anionic surfactant has a Krafft point of less than about 30 C.

3. The bar of claim 1 further comprising $C_{12-18}$ normal alkyl sulfonated methyl ester(s).

4. The bar of claim 1 further comprising a Lathering Index Ratio of more than about 0.8.

5. The bar of claim 1 further comprising cationic polymer(s).

6. The bar of claim 1 further comprising a pH of in the range of about 8.5 to 10.0.

7. The bar of claim 1 further comprising a safe and effective amount of at least one active agent, a hydrophilic moisturizing agent or blend thereof.

8. The toilet bar of claim 1 wherein the soaps include a blend of $C_6$ to $C_{22}$ alkyl soaps.

9. The bar of claim 1 further comprising water in the range of about 1 to less than about 15% by wt.

10. A method of skin treatment and/or cleansing with a combination toilet bar, comprising the steps of:

a. wetting the mild bar with water; the bar including:

1. about 50 to 80% by wt. of soap(s) wherein the soap(s) contain 15.6–24.9% by wt. of oleic soap;
2. about 1 to 5% by wt. of amphoteric surfactant(s);
3. about 1 to 5 by wt. of synthetic anionic surfactant(s);
4. about 0.1 to 10% of hydrophobic emollient(s) with a titer point between about 1 to 80 C other than a hydrocarbon with a titer less than about 50 C;
5. greater than about 0.1 to less than 2% by wt. of a hydrocarbon with a titer less than about 50 C;
6. wherein the ratio of synthetic anionic surfactants to amphoteric surfactant(s) is in the range of about 1 to 5 to 5 to 1; and b. rubbing the wet bar on the skin to deposit the emollients and/or skin active ingredients while cleansing the skin.

* * * * *